United States Patent [19]

Morikawa et al.

[11] Patent Number: 4,472,419

[45] Date of Patent: Sep. 18, 1984

[54] METHOD OF CONTROLLING PLANT NEMATODES

[75] Inventors: Osamu Morikawa, Kanagawa; Katsuaki Tadenuma, Tokyo; Osamu Taniguchi, Saitama, all of Japan; Irwin B. Wood, Pennington, N.J.

[73] Assignee: American Cyanamid Company, Stamford, Conn.

[21] Appl. No.: 572,790

[22] Filed: Jan. 25, 1984

[51] Int. Cl.$^3$ .................. A01N 43/78; A01N 43/80
[52] U.S. Cl. ................................................ 424/270
[58] Field of Search ....................................... 424/270

[56] References Cited

U.S. PATENT DOCUMENTS 4,009,266  2/1977  Ayalew .............................. 424/270
4,197,307  4/1980  Gallay et al. .................... 424/273 B

OTHER PUBLICATIONS

The Merck Index; Ninth Edition, (1976); #8949, Tetramisole.

Primary Examiner—Leonard Schenkman
Assistant Examiner—Joseph A. Lipovsky
Attorney, Agent, or Firm—Alphons R. Noë; Noë

[57] ABSTRACT

The present invention relates to a novel method for controlling nematodes in plants by applying to the plants, pesticidally-effective amounts of dl or l-6-phenyl-2,3,5,6-tetrahydroimidazo[2,1-b]thiazole, acylamino derivatives, or water-soluble acid salts thereof.

8 Claims, No Drawings

METHOD OF CONTROLLING PLANT NEMATODES

The present invention relates to a novel method for controlling nematodes in plants. This is done by applying to the plant pesticidally-effective amounts of dl or 1-6-phenyl-2,3,5,6-tetrahydroimidazo[2,1-b]thiazole, acylamino derivatives, as shown in formula (I), or the watersoluble acid salts of formula (I):

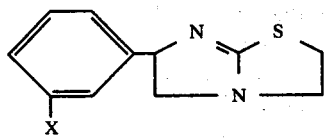

(I)

X is hydrogen or —NHR; R is $C_2$-$C_5$ alkanoyl or benzoyl.

Pinetree nematodes (*Bursaphelenchus lignicolus*) have caused and continue to cause great problems in certain areas of the world, such as Japan. These nematodes are causing the death of pinetrees over such wide areas ranging from southern to central Japan. Currently, the typical method used for the protection of pinetrees from damage by pinetree nematodes is to aerially spray an insecticide to control the pine sawyers (*Monochamus alternatus*) which carry the nematodes. While this kind of aerial spraying of insecticides attempts to prevent the spread of pinetree nematodes, generally, it does not provide specific control of the problem pest, the nematode itself.

Unexpectedly, it has been found that formula (I) compounds or the water-soluble acid salts thereof, are useful agents for the control of pinetree nematodes.

These present compounds even exhibit activity against the free-living soil nematode *C. elegans* and the vinegar eel *Turbatrix aceti*. Levamisole, (l-6-phenyl-2,3,5,6-tetrahydroimidazo[2,1-b]thiazole), tetramisole, (dl-6-phenyl-2,3,5,6-tetrahydroimidazo[2,1-b]thiazole), dl or (1-3'-(2,3,5,6-tetrahydroimidazo[2,1-b]thiazole-6yl-isobutyranilide hydrochloride), dl or (1-3'-(2,3,5,6-tetrahydroimidazo[2,1-b]thiazol-6-yl-benzanilide hydrochloride or water-soluble acid salts thereof, especially the hydrochloride or hydrosulfide, have been used as anthelimintic agents used for livestock and zoo animals. However, these compounds have not been used for control of plant nematodes.

Other plant nematodes which may also be controlled by the method of the present invention include those that infest crops such as: potato, (*Glabodera rostochiensis*); sweet potato, (*Meloidogyne incognita*); soybeans, (*Heterodera glycines*); eggplant and tomato, (*Meloidogyne hapla*); cucumber, melon and watermelon, (Meloidogyne spp. and *Pratylenchus penetrans*); radish, cabbage and chinese cabbage, (*M. incognita* and *P. coffeae*); onion and welsh onion, (Pratylenchus spp.); carrot, (Pratylenchus spp.); strawberries (*Nothotylenchus acris* and *Aphelenchoides fragariae*); tobacco, (Meloidogyne spp. and Pratylenchus spp.); chrysanthemum, (Pratylenchus spp., Meloidogyne spp. and *Aphelenchoides ritzemabosi*); rice, (*Aphelenchotes besseyi*); citrus, (Xiphinema spp. and Helicotylenchus); apple, (Pratylenchus spp. and Meloidogyne spp.); pear, (Pratylenchus spp.); peach, (Meloidogyne spp., Pratylenchus spp. and Xiphinema spp.); grape, (Meloidegyne spp., Pratylenchus spp., Xiphinema spp. and Helicotylenchus spp.); fig, (*Helicolyenchus erythrinea*); and tea, (Xiphinema spp. and Pratylenchus spp.).

Compositions containing formula (I) compounds or the water-soluble acid salts thereof for controlling pinetree nematodes can be formulated into either liquids or wettable powders. Liquid compositions include about 5% to 20%, w/w, of the active compound with appropriate amounts of a solvent such as methanol, ethanol, acetone, acetonitrile, and others, and the remainder, water. Wettable powders include about 5% to 20%, w/w, of the active compound, about 1% to 10% of surfactant, and inert carriers, such as clays, nemiculate, carbon black or the like.

Surfactants useful in the present invention include those commonly used for formulations of wettable powders, preferably alkylbenzene sulfonate sodium salts. Bentonite, clay or mixtures thereof are preferred carriers.

The compositions of the present invention can be applied to pinetrees as a preventative treatment, either by injection or by implantation of 1 to 20 grams of the active compound. Depending on the size of tree, the 1 to 20 grams of active compound should be placed either into the trunk of the pinetree or directly applied on the ground surrounding the tree. About 50 to 300 grams of active compound, with or without dilution with a suitable amount of water, should be placed within the root zone of the tree. Of course, the distance for applying the compound from the tree should be adjusted according to the size of tree.

Further illustration of the present invention is shown by the following non-limiting examples.

EXAMPLE 1

In vitro nematocidal activity of 1-6-phenyl-2,3,5,-tetrahydroimidazo[2,1-b]thiazole hydrochloride A wettable powder composition of the present invention was prepared using about 10% of the compound salt, 1-6-phenyl-2,3,5,6-tetrahydroimidazo[2,1-b]thiazole hydrochloride, about 5% of the surfactant alkylaryl sulfonate sodium salt, and about 85% bentonite.

Different aqueous concentrations of this wettable powder composition were formed by adding an appropriate amount of the wettable powder to 10 ml of water. Then, 3 ml of the thus prepared water solutions of the test chemical were pipetted into a test tube containing a 3 ml water-suspension of the pinetree nematodes. These pinetree nematodes were artificially cultured with Botrytis spp. These test tubes then were kept at 25° C. for 48 hours, and following the 48 hours, the resulting number of dead, paralyzed and normal nematodes were microscopically counted.

The results of these experiments are summarized in Table I.

TABLE I

| Concentration of the test chemical (ppm) | Percent of nematodes | | |
|---|---|---|---|
| | Normal | Paralyzed | Dead |
| 500.0 | 0.0 | 44.6 | 55.4 |
| 250.0 | 0.0 | 55.2 | 44.8 |
| 125.0 | 0.0 | 66.9 | 33.1 |
| 10.0 | 0.0 | 76.2 | 23.8 |
| 1.0 | 0.0 | 78.8 | 21.2 |
| 0.5 | 3.0 | 86.4 | 10.6 |
| 0.25 | 12.6 | 82.2 | 5.2 |
| Control | 100.0 | 0.0 | 0.0 |

As can be seen from the results in Table I, it is clear that the present invention inactivates nematodes even when used at very low concentrations.

EXAMPLE 2

In vivo nematocidal activity of 1-6-phenyl-2,3,5,6-tetrahydroimidazo[2,1-b]-thiazole hydrochloride implant treatment of pinetrees A liquid formulation was prepared using about 10% 1-6-phenyl-2,3,5,6-tetrahydroimidazo[2,1-b]-thiazole hydrochloride, about 10% methanol and about 80% water.

The thus-prepared liquid formulation was placed into 100 ml-plastic ampules. Holes of about 9 mm in diameter and about 5 cm depth were drilled in the trunks of twenty healthy red pinetrees having trunk diameter of from about 9 to about 12 cm. These holes were located about 1.5 meters above ground level. An ampule containing the liquid formulation was inserted into the holes of ten pinetrees with the remaining ten pinetrees serving as untreated control.

Then, additional holes were drilled in the 20 selected pinetrees and a 1 ml nematode suspension, containing 20 to 30 thousand pinetree nematodes, was inoculated into these holes 30 days later. Each hole had about a 9 mm diameter and was placed about 4 meters above ground level. Following the first treatment, the trees were evaluated for excretion of resin at 90 and 150 days, and mortality of the tree was checked at 150 days. The results of this experiment are summarized in Table II below:

TABLE II

| Treatment | No of Tree | Excretion of Resin 90 days | Excretion of Resin 150 days | Mortality of tree 150 days |
|---|---|---|---|---|
| Treated | 1 | +++ | +++ | Alive |
|  | 2 | +++ | +++ | Alive |
|  | 3 | ++ | ++ | Alive |
|  | 4 | +++ | +++ | Alive |
|  | 5 | +++ | +++ | Alive |
|  | 6 | +++ | +++ | Alive |
|  | 7 | ++ | ++ | Alive |
|  | 8 | + | — | Alive |
|  | 9 | +++ | +++ | Alive |
|  | 10 | +++ | +++ | Alive |
| Control | 11 | — | — | Dead |
|  | 12 | + | — | Dead |
|  | 13 | — | — | Dead |
|  | 14 | — | — | Dead |
|  | 15 | — | — | Dead |
|  | 16 | — | — | Dead |
|  | 17 | — | — | Dead |
|  | 18 | + | — | Dead |
|  | 19 | — | — | Dead |
|  | 20 | — | — | Dead |

+++ = normal resin excretion - same as healthy trees
++ = resin excretion 50% to 80% of healthy trees
+ = resin excretion less than 50% of healthy trees
— = no resin excretion The results shown in Table II indicate that implants containing the present invention were effective in protecting pinetrees from nematode causing mortality.

EXAMPLE 3

In vivo soil treatment of pinetrees

The wettable powder formulation prepared according to Example 1 was applied onto the soil surface of potted (15 cm diameter pots) three-year-old black pinetrees; about 0.2 gram of the active compound was added to each pot. Twenty days following treatment, pinetree nematodes were inoculated onto the branch tips of the trees.

Two months after the inoculation of nematodes onto the pinetree branches, the number of dead pinetrees were counted, and the results of this experiment are summarized in Table III below:

TABLE III

| Treatment | No of trees used | No of dead pinetrees | Percent of dead pinetrees |
|---|---|---|---|
| Treated | 20 | 4 | 20 |
| Untreated | 15 | 15 | 100 |

Again, in vivo testing of the present invention result in a significant decrease of the mortality rate of treated vs. untreated pinetrees (20% in comparison to 100%).

EXAMPLE 4

In vitro activity against Turbatrix aceti

Each chemical, indicated in Table IV, tested was dissolved in water to provide appropriate concentrations of 1 to 1000 ppm of active compound. A 0.1 ml aliquot of the appropriate concentration was then added to 0.1 ml of an apple cider containing bakers yeast culture containing mixed developmental stages of Vinegar eelworm (*Turbatrix aceti*).

The effectiveness of each compound was determined by comparing the behavior of the treated nematodes to those not treated (control). Rating of nematode activity was based upon movement, particularly surface movement, since all stages of *Turbatrix aceti* spend the vast majority of their time actively swimming on the surface of the apple cider medium. This rating system is provided below:

Rating System

| Rating | Effect |
|---|---|
| F | Few moving |
| M | Many moving |
| NM | No movement |
| AM | Abnormal movement |
| SM | Slight movement |
| O | None on surface |

The compounds of the present invention initially inhibited the ability of the nematodes to remain on the surface of the medium. Within four hours, 1 ppm of levamisole inhibited all stages of *Turbatrix aceti*. The effect progressed in intensity over time, and by 72 hours, no movement was detected in the wells containing levamisole at 1000, 100, 10 or 1 ppm. A summary of the results is tabulated in Table IV:

TABLE IV

Activity against *Turbatrix aceti* of Formula (I) compounds having the structure

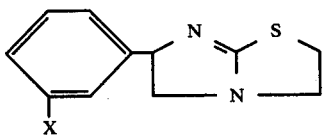

| Formula I Compound | | Location of T. aceti | Activity against T. aceti time concentration ppm | | | | | | | | | | | |
|---|---|---|---|---|---|---|---|---|---|---|---|---|---|---|
| Optical isomer | X | in medium | 5–10 minutes | | | | 24 hours | | | | 48 hours | | | |
| | | | 1000 | 100 | 10 | 1 | 1000 | 100 | 10 | 1 | 1000 | 100 | 10 | 1 |
| l | H | surface | F | F | M | M | O | O | F | F | O | O | O | F |
| | | bottom | M | M | F | F | NM | AM | M | M | M | SM | SM | AM |
| dl | NH$_2$ | surface | O | F | M | M | O | O | O | F | O | O | O | F |
| | | bottom | M | M | F | F | NM | SM | SM | SM | SM | SM | SM | SM |
| dl | —NH—⟨phenyl⟩ | surface | F | M | M | M | O | O | O | F | O | O | O | F |
| | | bottom | M | F | F | F | NM | M | M | M | NM | SM | SM | AM |
| Untreated controls | | surface | | M | | | | M | | | | M | | |
| | | bottom | | F | | | | F | | | | F | | |

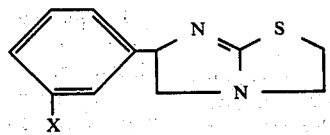

| Formula I Compound | | Location of T. aceti | Activity against T. aceti time concentration ppm | | | | | | | |
|---|---|---|---|---|---|---|---|---|---|---|
| Optical isomer | X | in medium | 36 hours | | | | 72 hours | | | |
| | | | 1000 | 100 | 10 | 1 | 1000 | 100 | 10 | 1 |
| l | H | surface | O | O | O | O | O | O | O | O |
| | | bottom | NM | SM | SM | SM | NM | NM | NM | NM |
| dl | NH$_2$ | surface | O | O | O | F | O | O | — | — |
| | | bottom | NM | SM | SM | SM | NM | NM | NM | NM |
| dl | —NH—⟨phenyl⟩ | surface | O | O | O | F | O | O | O | O |
| | | bottom | NM | SM | AM | AM | NM | AM | AM | AM |
| Untreated controls | | surface | | M | | | | M | | |
| | | bottom | | F | | | | F | | |

EXAMPLE 5

**In vitro nematocidal activity against the soil nematode *Caenorhabditis elegans***

Several formula (I) compounds, listed in Table V, were dissolved in sufficient amounts of water to provide 0.1 to 1000 ppm of active compound when 0.1 ml aliquots of the aqueous solutions were added to 0.1 ml of *C. briggsae* medium containing *C. elegans*.

The compounds' effects were observed over time (2, 24 and 48 hours) and assigned ratings using the rating system provided below:

| Rating | Rating System Effect |
|---|---|
| ++++ | Nematodes contracted and paralyzed - No movement |
| +++ | Markedly reduced movement |
| ++ | Abnormal movement |
| ± | Reduced movement in some nematodes |

The results of this example, summarized in Table V below, clearly demonstrate the effectiveness of the present invention in controlling nematodes.

TABLE V

Nematocidal activity against *C. elegans* of Formula (I) compounds having the structure:

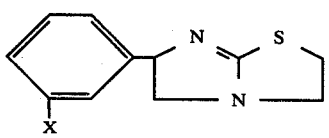

| Optical isomer | Formula (I) compound X | Time Post immersion (hours) | Adverse effect at concentration (ppm) | | | |
|---|---|---|---|---|---|---|
| | | | 100 | 10 | 1 | 0.1 |
| L | H | 2 | ++++ | +++ | ++ | ± |
| | | 24 | ++++ | ++++ | +++ | ± |
| | | 48 | ++++ | +++ | +++ | ± |
| dl | NH₂ | 2 | — | ++++ | +++ | ± |
| | | 24 | — | ++++ | ++++ | +++ |
| | | 48 | — | ++++ | ++++ | +++ |
| dl | H —N—⟨⟩ | 2 | ++++ | ++++ | +++ | ++ |
| | | 24 | ++++ | ++++ | ++++ | +++ |
| | | 48 | ++++ | ++++ | ++++ | ++++ |

++++ = Nematodes contracted and paralyzed - no movement
+++ = Nematodes contracted and paralyzed - markedly reduced movement
++ = Nematodes contracted and paralyzed - abnormal movement
± = Reduced movement in some nematodes
— = No test

What is claimed is:

1. A method for the control of plant nematodes comprising: applying to the foliage or onto the surrounding soil or into the trunk of a plant, a pesticidally effective amount of a compound or the water-soluble acid salts thereof having the structure;

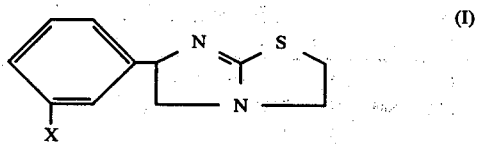

wherein X is hydrogen or —NHR; R is C₂–C₅ alkanoyl or benzoyl.

2. A method according to claim 1, wherein said compound is the l or dl optical isomer.

3. A method according to claim 2, wherein said compound is 1-6-phenyl-2,3,5,6-tetrahydroimidazo-[2,1-b]thiazole.

4. A method according to claim 2 wherein the compound is dl-6-phenyl-2,3,5,6-tetrahydroimidazo-[2,1-b]thiazole.

5. A method according to claim 2, wherein the compound is 1-6-phenyl-2,3,5,6-tetrahydroimidazo-[2,1-b]thiazole hydrochloride.

6. A method according to claim 2, wherein the compound is 1 or dl-3′(2,3,5,6-tetrahydroimidazo-[2,1-b]thiazol-6-yl-isobutyranilide hydrochloride.

7. A method according to claim 2, wherein the compound is 1 or dl-3′(2,3,5,6-tetrahydroimidazo-[2,1-b]thiazol-6-yl-benzanilide hydrochloride.

8. A method according to claim 2, wherein about 0.25 to 500 ppm of said compound is applied by injection, implantation or as a soil treatment.

* * * * *